(12) United States Patent
Aldrich et al.

(10) Patent No.: US 7,430,449 B2
(45) Date of Patent: Sep. 30, 2008

(54) METHODS AND APPARATUS FOR TESTING DISRUPTION OF A VAGAL NERVE

(75) Inventors: William N. Aldrich, Napa, CA (US); David Miller, Palo Alto, CA (US)

(73) Assignee: EndoVx, Inc., Napa, CA (US)

( * ) Notice: Subject to any disclaimer, the term of this patent is extended or adjusted under 35 U.S.C. 154(b) by 356 days.

(21) Appl. No.: 11/067,185

(22) Filed: Feb. 24, 2005

(65) Prior Publication Data
US 2005/0240231 A1 Oct. 27, 2005

Related U.S. Application Data

(63) Continuation-in-part of application No. 10/389,236, filed on Mar. 14, 2003.

(51) Int. Cl.
*A61N 1/36* (2006.01)
(52) U.S. Cl. ....................................... 607/40
(58) Field of Classification Search ................... 607/40, 607/118; 600/554, 561, 350
See application file for complete search history.

(56) References Cited

U.S. PATENT DOCUMENTS

| | | | |
|---|---|---|---|
| 3,128,760 A * | 4/1964 | Baker | 600/554 |
| 5,188,104 A | 2/1993 | Wernicke et al. | |
| 5,263,480 A * | 11/1993 | Wernicke et al. | 607/118 |
| 5,471,988 A | 12/1995 | Fujio et al. | |
| 5,807,285 A | 9/1998 | Vaitekunas et al. | |
| 5,878,749 A | 3/1999 | Miller | |
| 6,197,022 B1 | 3/2001 | Baker | |
| 6,405,732 B1 * | 6/2002 | Edwards et al. | 128/898 |
| 6,427,089 B1 * | 7/2002 | Knowlton | 607/101 |
| 6,591,137 B1 * | 7/2003 | Fischell et al. | 607/40 |
| 6,609,025 B2 * | 8/2003 | Barrett et al. | 607/2 |

(Continued)

FOREIGN PATENT DOCUMENTS

WO   WO 00/69376   11/2000

(Continued)

OTHER PUBLICATIONS

Bell, P.R.F., The Long Term Effect Of Vagotomy On the Maximal Acid Response To Histamine In Man, Univ. Dept. of Surgery, Royal Infirmary, Sheffield, England, vol. 46, No. 4, pp. 387-391, 1963.

(Continued)

*Primary Examiner*—Carl H. Layno
*Assistant Examiner*—Jon-Eric C. Morales
(74) *Attorney, Agent, or Firm*—Orrick, Herrington & Sutcliffe LLP

(57) ABSTRACT

Method and apparatus for disrupting a gastric vagal nerve in the gastroesophageal region and testing the function and disruption of the vagal nerve. In one example embodiment, a treatment device applies ultrasound at a high energy level, such as high intensity focused ultrasound, to a vagal nerve to disrupt it and then ultrasound at a lower energy level to another portion of the vagal nerve, preferably further from the stomach, so as to stimulate the vagal nerve. Alternative ways to test the function or disruption of the vagal nerve involve using PCP-GABA, a pancreatic polypeptide, pressure changes inside the stomach, the gastric mucusol pH, a dye agent in the stomach, and other tests.

32 Claims, 14 Drawing Sheets

U.S. PATENT DOCUMENTS

| | | | |
|---|---|---|---|
| 6,826,428 B1* | 11/2004 | Chen et al. .................... 607/40 |
| 7,160,258 B2* | 1/2007 | Imran et al. ................. 600/593 |
| 2002/0032468 A1* | 3/2002 | Hill et al. ....................... 607/2 |
| 2002/0087192 A1* | 7/2002 | Barrett et al. .................. 607/2 |
| 2002/0103424 A1* | 8/2002 | Swoyer et al. ............. 600/350 |
| 2002/0198470 A1* | 12/2002 | Imran et al. ................. 600/587 |
| 2003/0023287 A1 | 1/2003 | Edwards et al. |
| 2003/0028111 A1 | 2/2003 | Vaezy et al. |
| 2003/0144708 A1* | 7/2003 | Starkebaum ................ 607/40 |
| 2004/0082859 A1 | 4/2004 | Schaer |
| 2004/0181178 A1 | 9/2004 | Aldrich et al. |
| 2004/0186468 A1 | 9/2004 | Edwards |
| 2005/0021101 A1* | 1/2005 | Chen et al. .................... 607/40 |

FOREIGN PATENT DOCUMENTS

| | | |
|---|---|---|
| WO | WO 01/00273 A1 | 1/2001 |
| WO | WO 01/22897 A1 | 4/2001 |

OTHER PUBLICATIONS

Burge, H. et al., Method Of Testing For Complete Nerve Section During Vagotomy, British Medical Journal, Mar. 15, 1958, pp. 615-618.

Burge, H. et al., The Technique Of Bilateral Selective Vagotomy With The Electrical Stimulation Test, Brit. J. Surg., vol. 56, No. 6, Jun. 1969, pp. 452-460.

Date, Y. et al., The Role of the Gastric Afferent Vagal Nerve in Ghrelin-Induced Feeding and Growth Hormone Secretion in Rats, Gastroenterology 2002; 123: 1120-1128.

Date, Y. et al., Ghrelin Acts in the Central Nervous System to Stimulate Gastric Acid Secretion, Biochem. and Biophys. Res. Communications, 280, 904-907 (2001).

Goto, Y. et al., A New Intraoperative Test for Completeness of Vagotomy: The PCP-GABA (Beta-Parachlorophenol-Gamma-Aminobutyric Acid) Test, The American J. of Surgery, vol. 147, Jan. 1984, pp. 159-163.

Grassi, G. et al., Intraoperative Relation Of Gastic Secretion Acidity And Complete Vagotomy, Surgery, Gynecology & Obstetrics, vol. 134, Jan. 1972, pp. 35-38.

Hennessy, T.P.J. et al., An improved preoperative test of vagal section, Annals of the Royal College of Surgeons of England, vol. 61, 1979, pp. 474-476.

Kral, J.G. et al., Gastroplasty for Obesity: Long-Term Weight Loss Improved by Vagotomy, World J. Surg. 17, 75-79 (1993).

Kral, J. G., Surgical Treatment of Obesity, Medical Clinics of North America, vol. 73, No. 1, Jan. 1989.

Kral, J.G., Behavioral effects of vagotomy in humans, J. of Autonomic Nervous System, 9 (1983) 273-281.

Kral, J.G. et al. Truncal vagotomy in morbid obesity, Int'l J. Obesity (1981) 5, 431-435.

Nagammapudur, S. et al., A Safe and Noninvasive Test for Vagal Integrity Revisited, Arch. Surg., vol. 137, Aug. 2002, pp. 954-957.

Ross, B. et al., The Insulin Test After Vagotomy, The Univ. Dept. of Surgery, The Royal Infirmary, Sheffield, England, vol. 46, No. 4, pp. 379-386, 1963.

* cited by examiner

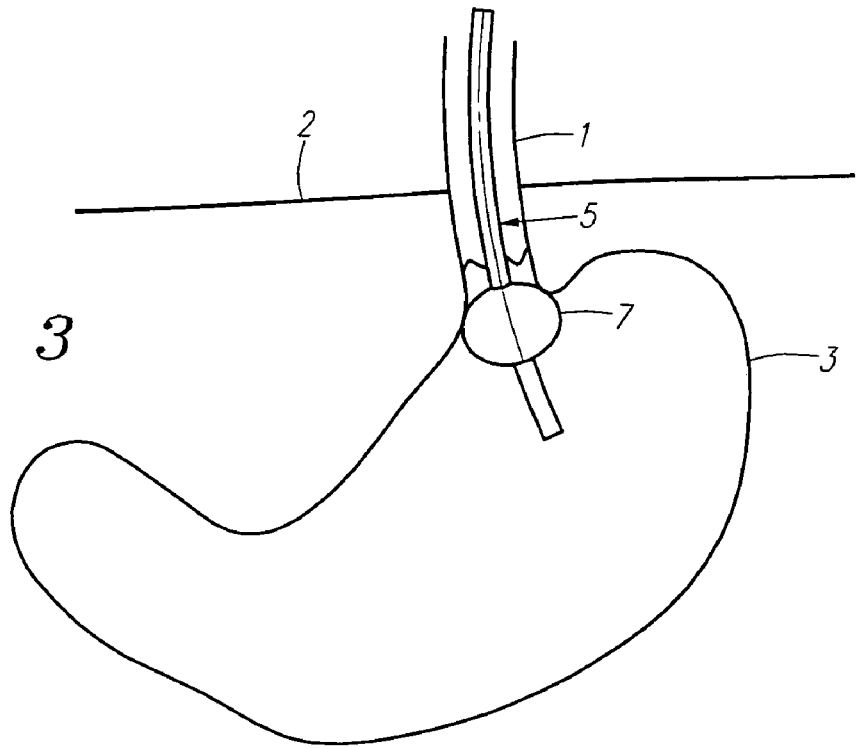
FIG. 3 — BALLOON POSITIONING - SINGLE LOWER
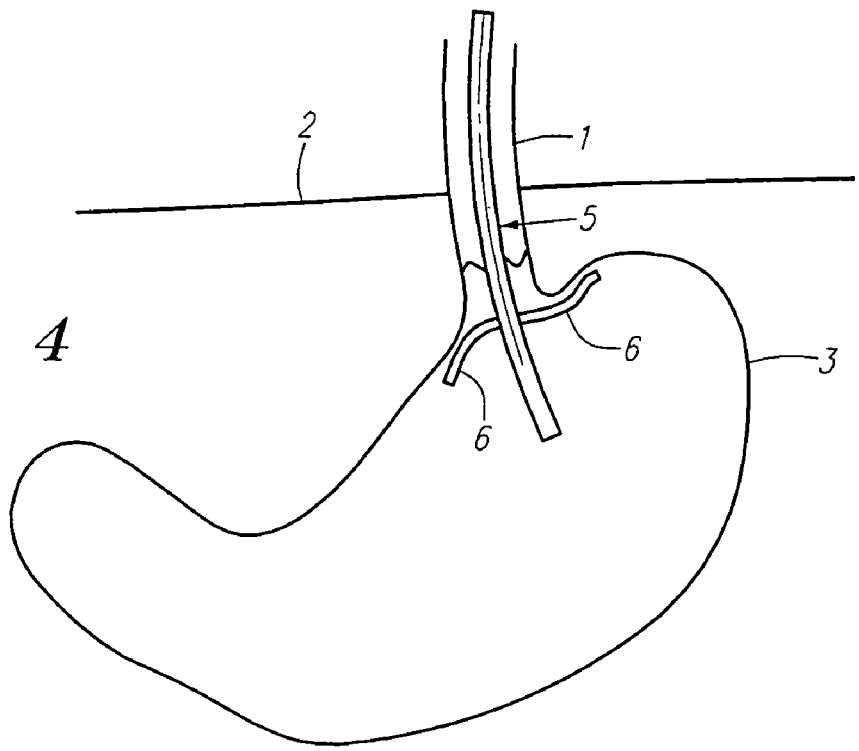
FIG. 4 — FEET POSITIONING BITE BLOCK
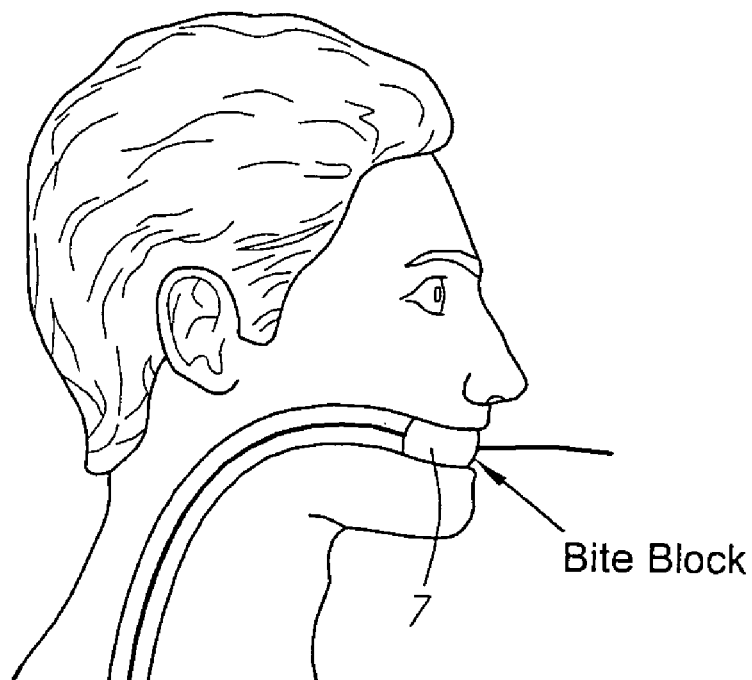
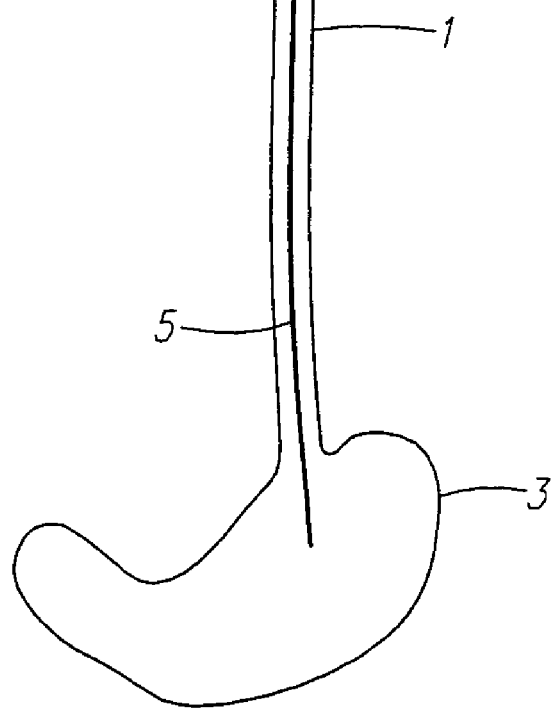
FIG. 5

COMPLETE CIRCUMFERENCE ABLATION

SECTOR SCAN/ABLATION

DEVICE WITH UNDEPLOYED BALLOONS

DEVICE WITH DEPLOYED BALLOONS

Section View of Device

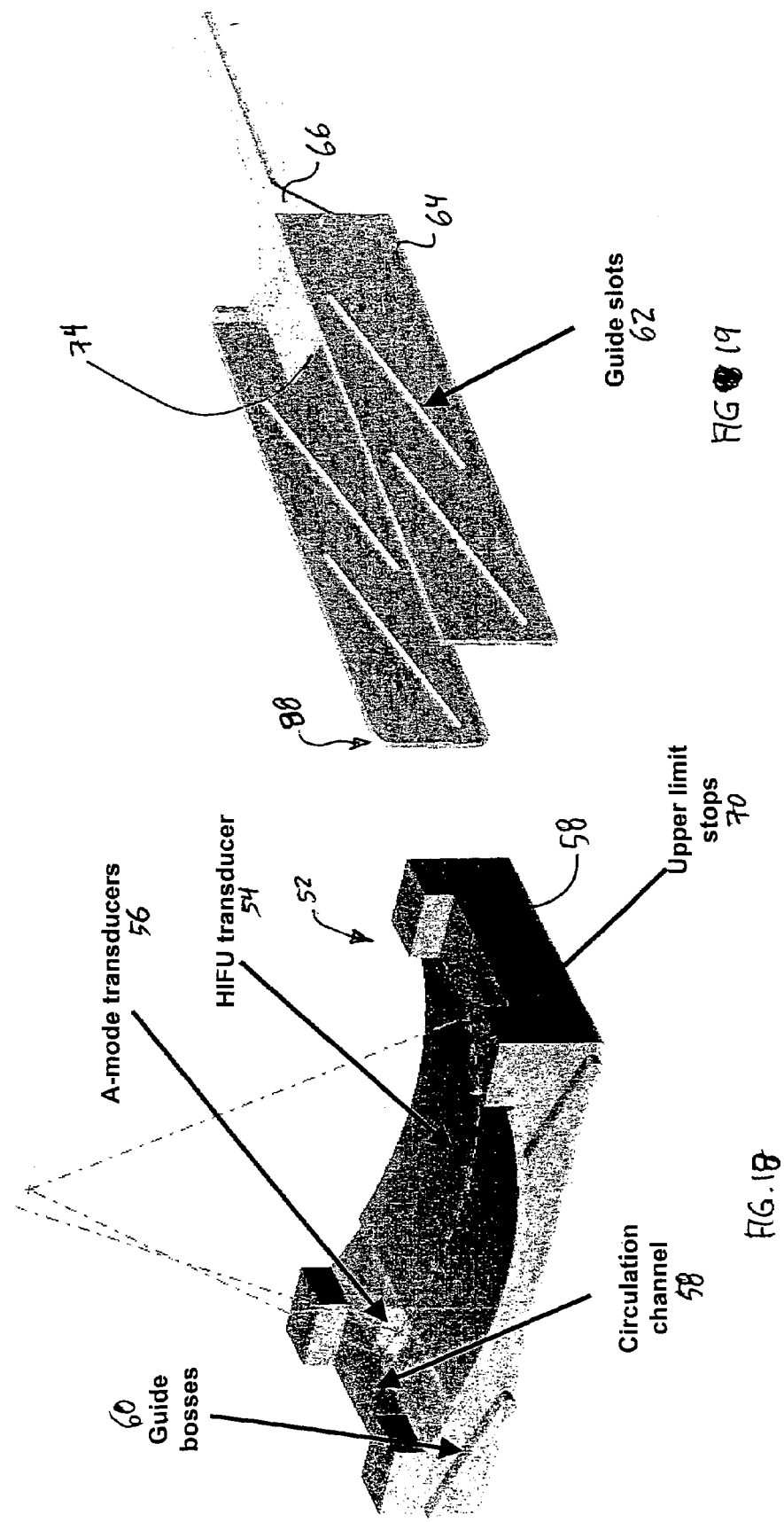

METHODS AND APPARATUS FOR TESTING DISRUPTION OF A VAGAL NERVE

CROSS REFERENCE TO RELATED PATENT APPLICATIONS

This application is a continuation-in-part of U.S. patent application Ser. No. 10/389,236, titled "Methods and Apparatus for Treatment of Obesity," filed Mar. 14, 2003.

FIELD OF THE INVENTION

The field of the present invention is methods and devices for treating obesity, and more particularly, methods and devices for disrupting a vagal nerve and testing the disruption of the function of the vagal nerve.

BACKGROUND OF THE INVENTION

Obesity has become an ever-increasing health problem. While such voluntary weight reduction programs as dieting and exercise have been helpful for some, many obese persons have required surgery to address their obesity problem. Two such surgical procedures are vertical banded gastroplasty (VBG) and the Roux-en-Y gastric bypass procedure. Both such procedures are now well known, but they are invasive in nature and involve reducing the size of the stomach. The parent patent application describes novel methods and devices for treating obesity by disrupting the vagal nerve. Because an incompletely disrupted vagal nerve still control appetite and certain stomach functions, there is a need to test the function and disruption of the vagal nerve.

SUMMARY OF THE INVENTION

The preferred embodiment of the present invention uses an elongate device that outputs energy to disrupt the function of the vagal nerve from within the esophagus and then applies at least one of a variety of tests to determine whether the vagal nerve has been disrupted. By monitoring the stomach, such as monitoring for changes in pressure in the stomach or the gastric mucusol pH, one may determine whether the vagal nerve has been disrupted. Alternative methods for testing the completeness of the vagotomy include using a pancreatic polypeptide such as PCP-GABA, a dye agent such as Congo Red, the Burge test, the Grassi test, augmented histamine test, a neurotransmitter amino acid, and other tests described later in this application. An example embodiment uses a treatment device capable of outputting two different energy levels. The treatment device preferably outputs at a high energy level sufficient to disrupt a vagal nerve. Then the physician moves the treatment device to another location, preferably at a location further from the stomach, and applies a low energy level sufficient to stimulate the vagal nerve without disrupting the nerve. An alternative to using the treatment device to output a low energy level, other devices may apply an electrical voltage to stimulate the vagal nerve.

Other systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims. It is also intended that the invention is not limited to require the details of the example embodiments.

DESCRIPTION OF THE DRAWINGS

The details of the invention, including fabrication, structure and operation, may be gleaned in part by study of the accompanying figures, in which like reference numerals refer to like segments. The figures are not to scale and the size of the features in relation to each other is not intended to limit the invention in any way.

FIG. 3 illustrates positioning the ablation device using a balloon which is inflated in the stomach.

FIG. 4 illustrates a positioning device using radially extending feet.

FIG. 5 illustrates a positioning device using a bite block.

FIG. 18 illustrates a perspective view of a preferred embodiment of the transducer platform.

FIG. 19 illustrates a perspective view of a preferred embodiment of a position actuator.

DETAILED DESCRIPTION OF THE INVENTION

Before turning to the manner in which the present invention functions, it is believed that it will be useful to briefly review the anatomy of the stomach and the esophagus. The esophagus is a muscular tube that carries food from the throat to the stomach and which passes through the diaphragm. The top end of the esophagus is the narrowest part of the entire digestive system and is encircled by a sphincter (circular muscle) that is normally closed but can open to allow the passage of food. There is a similar sphincter at the point where the esophagus enters the stomach. The walls of the esophagus consist of strong muscle fibers arranged in bundles, some circular and others longitudinal. The inner lining of the esophagus consists of smooth squamous epithelium (flattened cells).

Figure 1:
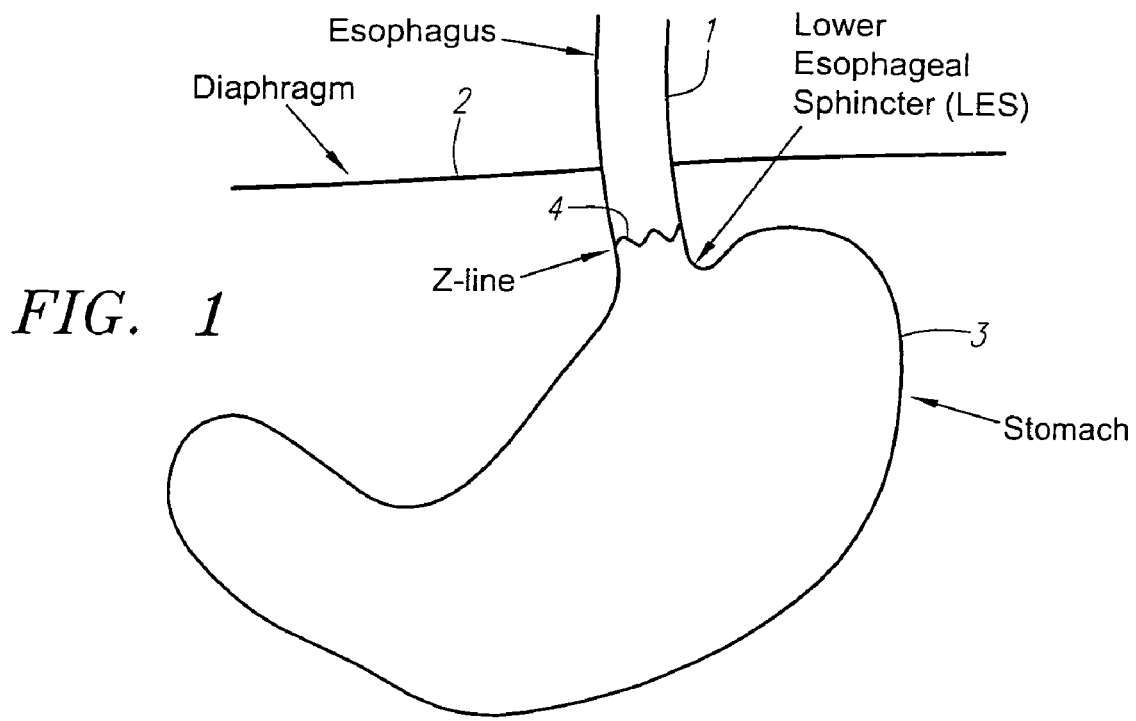
FIG. 1 is a diagrammatic illustration of the general anatomy of the stomach and esophagus.

As shown in FIG. 1, the esophagus 1 extends through the diaphragm 2 into the stomach 3. Vagal nerve branches extend from the stomach along the outer wall of the esophagus to the brain. At the lower end of the esophagus, the juncture of the esophageal and gastric mucosa forms a zig-zag line 4, usually referred to as the Z-line. In the area extending from the diaphragm to a point below the Z-line, there is a subhiatal fat ring which surrounds the outer wall of the esophagus. The vagal nerve branches run between the outer wall of the esophagus and the hiatal fat ring in this area. This anatomy is well understood by those skilled in the art and a more detailed description can readily be found in a standard work such as *Gray's Anatomy*.

It appears that a hunger signal is expressed by ghrelin, a peptide primarily produced in the stomach, and transmitted to the brain through the vagal nerve. The literature e.g., "The Role of the Gastric Afferent Vagal Nerve in Ghrelin-Induced Feeding and Growth Hormone Secretion in Rats," *Gastroenterology* 2002:123:1120-1128 (October 2002) by Yukari Date et al. and "Gastroplasty for Obesity: Long-term Weight Loss Improved by Vagotomy," *World Journal of Surgery*, Vol. 17, No. 1, January/February 1993, by Kral et al., supports this theory. The Date et al. article concluded that blockade of the gastric vagal afferent abolished ghrelin-induced feeding in rats and the Kral et al. article concluded that vagotomy combined with gastroplasty was more effective in controlling weight loss than gastroplasty alone. These articles are incorporated by reference herein.

The parent patent application treats obesity by interrupting the vagal nerve, preferably in the region of the esophagus, by minimally or noninvasive means. The vagal nerve branches may be disrupted in a transesophageal manner by using various types of energy including radio frequency (RF) energy, high intensity ultrasound, high intensity focused ultrasound, and other types of energy as described in more detail below. The energy source may be installed in the esophagus through the throat, but nasogastric access through the nose and extracorporeal application are also contemplated. The energy may be delivered to the vagal nerve through the esophagus wall, e.g., when ultrasound is used, or by causing an energy delivery device, e.g., an electrode to be passed through the wall of the esophagus.

Typically, there are two main branches, or trunks, of the vagal nerve which are located approximately 180° from each other on the outer wall of the esophagus. Depending on patient needs, it may be sufficient to interrupt only a portion of the fibers in the nerve. In this regard, it is to be noted that, in general, myelinated vagal nerve fibers, i.e., fibers that have an outer coating, are efferent. In contrast, afferent vagal nerves are unmyelinated and have no outer covering. For some patients, it may be sufficient to interrupt the function of only the afferent vagal fibers.

Still other energy sources can be used to interrupt the function of the vagal nerves including thermal, microwave, laser and cryogenic energy. Alternatively, the vagal nerve function can be interrupted by transesophageal delivery of a neurotoxin such as capsaicin, atropine, or botulinum toxin. Still further, mechanical means can be used to crush the vagal nerve, e.g., with a clip or pincer, or the vagal nerve can be cut transesophageally with an appropriate cutting instrument. In a preferred embodiment of the present invention, the vagal nerve will be interrupted in the vicinity of the zig-zag line, also known as the Z-line, which is generally located in the lower esophagus between the cardiac notch of the stomach and the diaphragm. However, the invention can be used to disrupt the vagal nerve at other locations, such as at the diaphragm.

The objective is, of course, weight loss by the patient as a result of interruption of efferent gastric and afferent hormonal signals transmitted through the vagal nerve branches. Thus, the success of the procedure described herein will, to some extent, be patient-dependent and, in some patients, it may be necessary to interrupt both the afferent and efferent vagal fibers, both of which may be found in the posterior and anterior branches.

Figure 2:
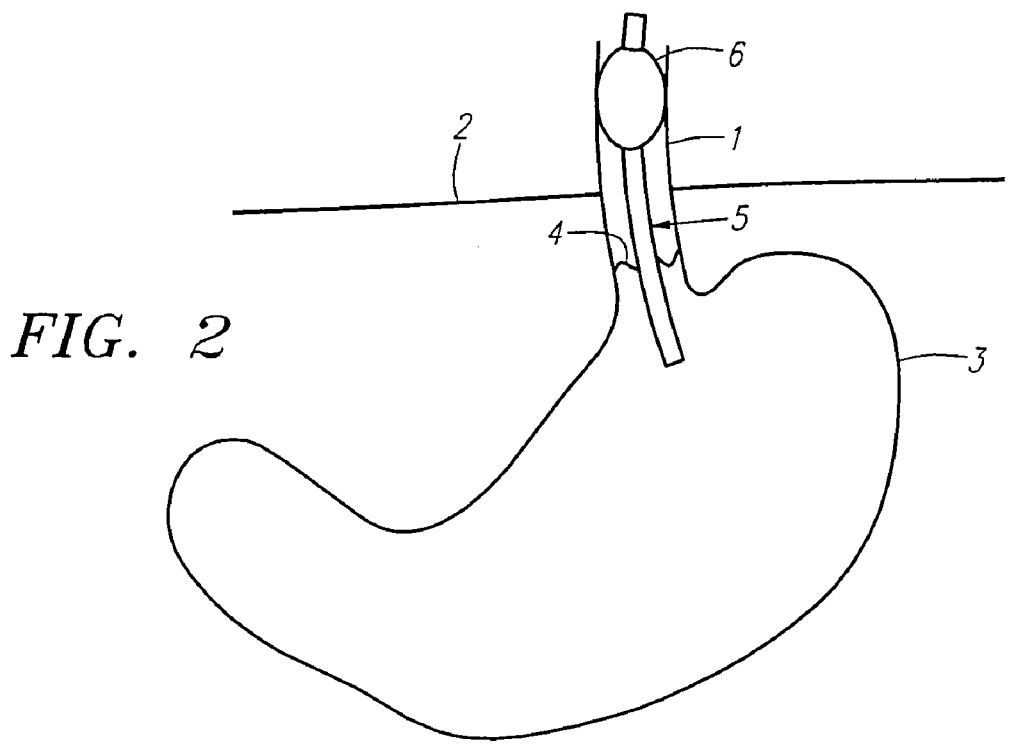
FIG. 2 illustrates positioning of an ablation device using a single balloon installed above the diaphragm.
Figure 6:
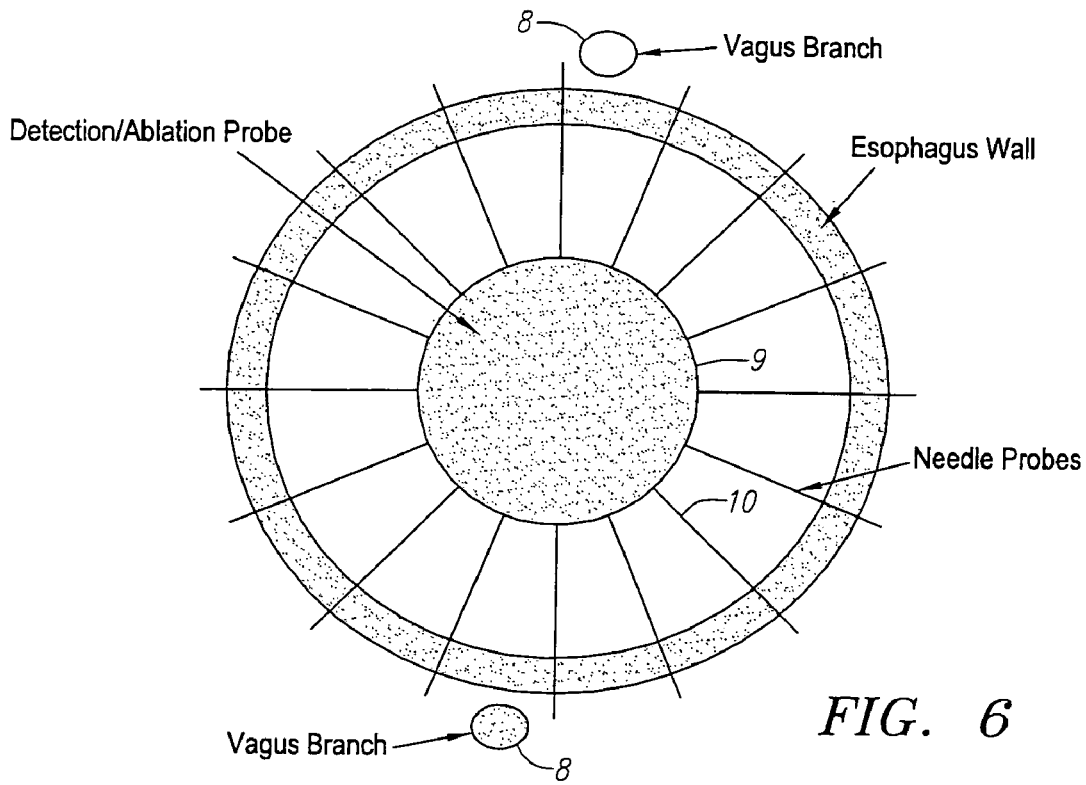
FIG. 6 is a diagrammatic illustrate of the use of needles or electrodes to detect and ablate around the circumference of the outer surface of the esophagus in a manner designed to interrupt all vagal nerve branches.

FIG. 2 illustrates in a diagrammatic manner an ablation device 5 which is held in place by balloon 6 which is inflated inside the upper portion of the esophagus. FIG. 3 illustrates positioning the ablation device 5 with balloon 7 which is inflated inside stomach 3. FIG. 4 illustrates positioning the ablation device 5 with feet 6 which pass through the esophagus folded against the ablation device 5 and then are extended inside stomach 3. FIG. 5 illustrates the use of a bite block 7 to position the ablation device 5 in stomach 3. FIG. 6 is a diagrammatic transverse cross section of the esophagus showing, in diagrammatic form, the esophagus wall 1, vagal nerve branches 8, a detection/ablation device 9 having needle probes 10. As shown, the needle probes 10 extend through the wall of the esophagus and can be used both to locate the vagus nerve and to ablate it. For detection purposes, the needle probes 10 are connected to an exterior control unit that detects and displays nerve activity in a manner well known to those skilled in the art. Once a vagal nerve is detected by a needle probe by sensing the activity of the nerve upon contact, the adjacent needle probes are energized and act in the manner of bipolar cautery probes which ablate the nerve and any other tissue between the needle probes. Preferably, the needle probes are designed in such a manner that they are held within the body of the ablation device until the device reaches its desired location. The needle probes can then be extended to penetrate the wall of the esophagus once the device has been positioned. Preferably, the needle probes are designed so that the electric current flows only at their tips so that the depth of the cautery can be focused to minimize damage to the esophagus. Cosman U.S. Pat. No. 4,565,200, Rydell U.S. Pat. No. 5,007,908, Edwards U.S. Pat. No. 5,370,675 and Edwards U.S. Pat. No. 6,129,726, each of which is incorporated by reference herein, disclose various types of electrode needle probe devices which can be used to deliver RF energy to tissue located within the body. Each of these patents discloses a device in which the needle probes are contained within the device until it has reached its desired location, at which time the needle probes are deployed to contact the tissue to which energy is to be delivered.

Figure 7:
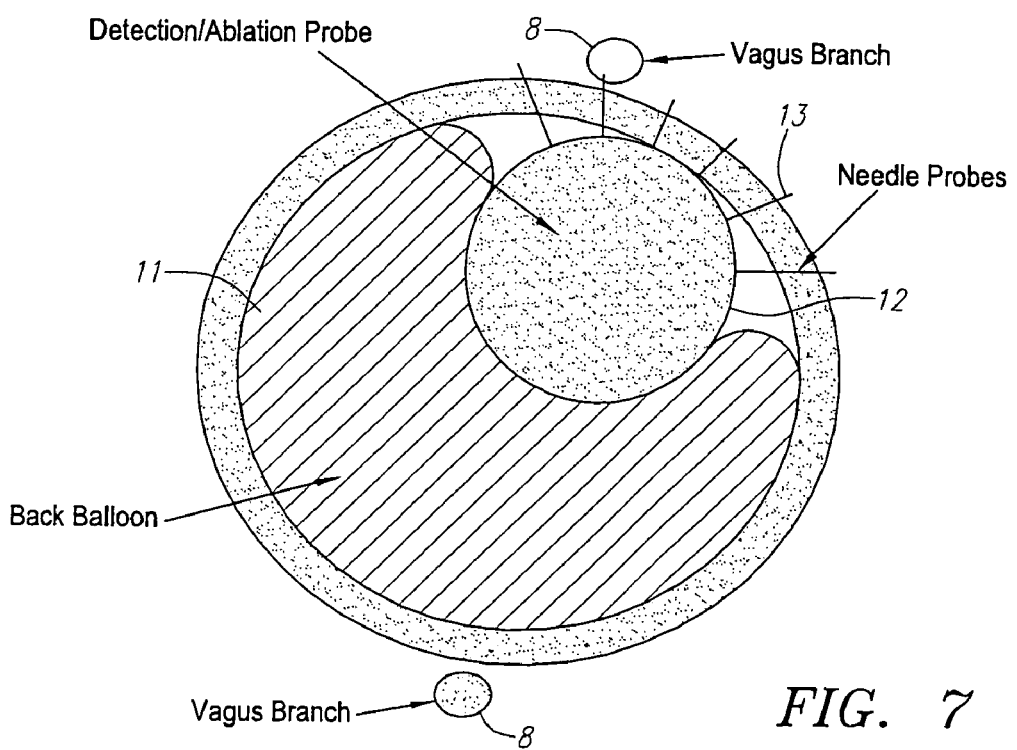
FIG. 7 is an illustration of an ablating device which ablates a sector of the circumference of the outer wall of the esophagus.

In the present invention, the needle probes can irradiate around the complete circumference of the device as shown in FIG. 6 or from only a portion of the device as shown in FIG. 7. If the latter, the device can be rotated sequentially to ensure complete coverage. As further shown in FIG. 7, when the needle probes 13 radiate from only a portion of the circumference of the device 12, a back balloon 11 can be used to position the device 12 in the desired location.

Figure 8:
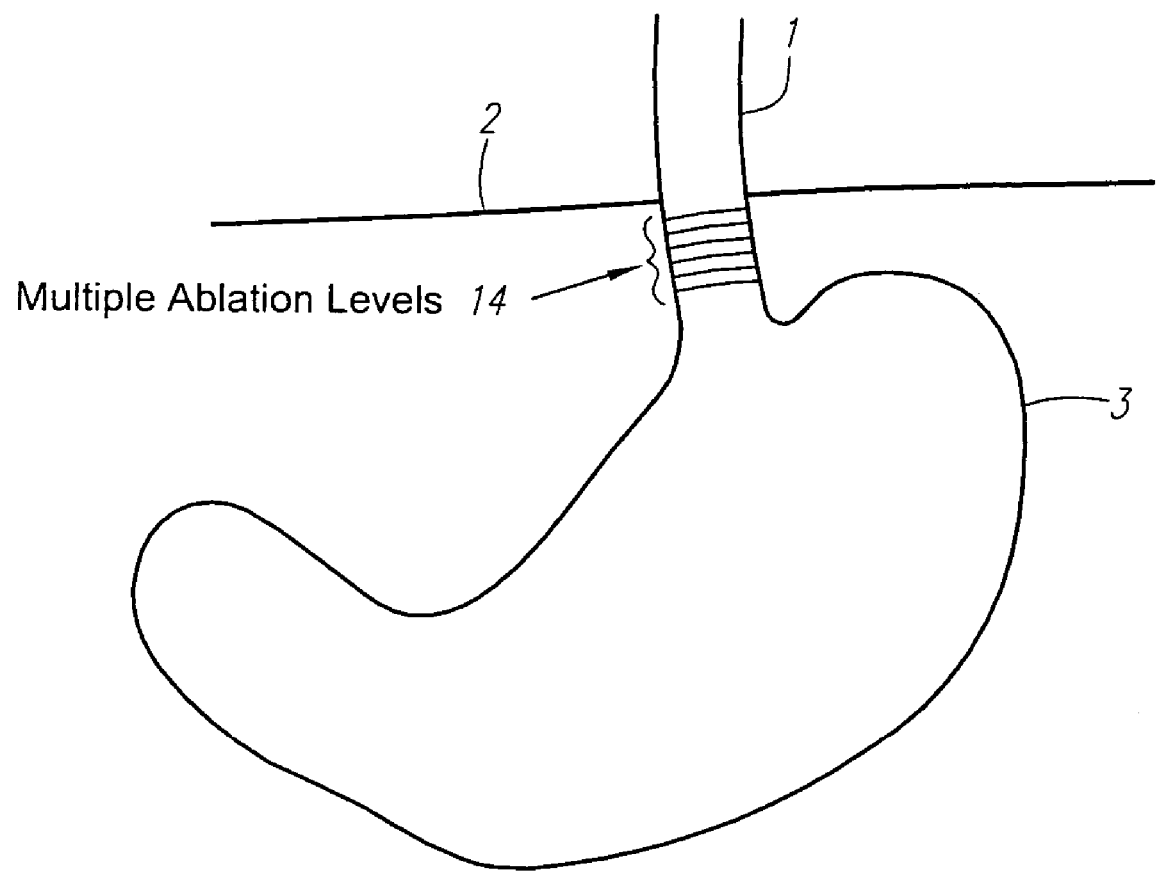
FIG. 8 shows ablating at multiple levels.
Figure 9:
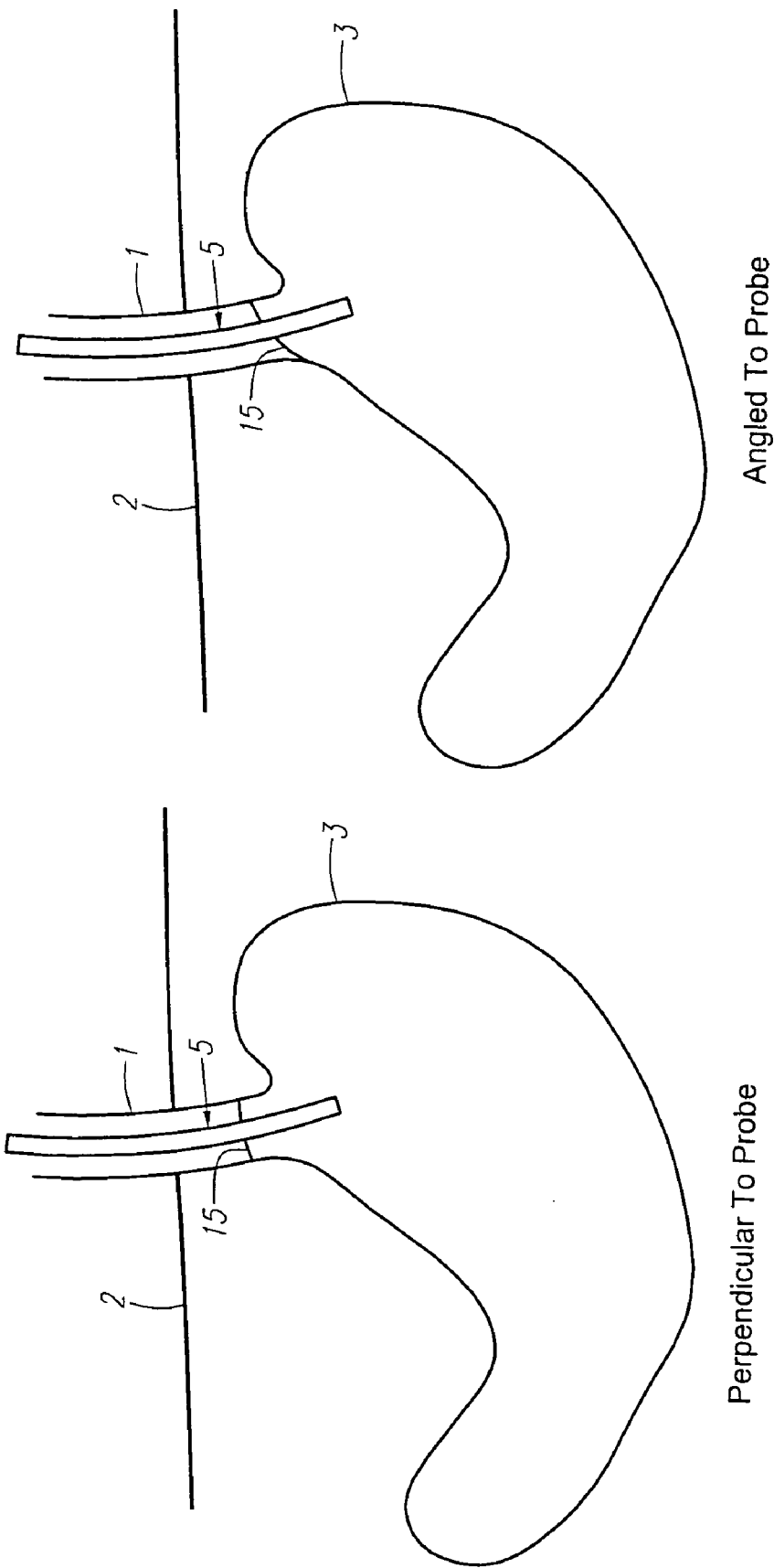
FIG. 9 illustrates an ablation ring which can be adjusted to ablate at different angles relative to the access of the esophagus.
Figure 10:
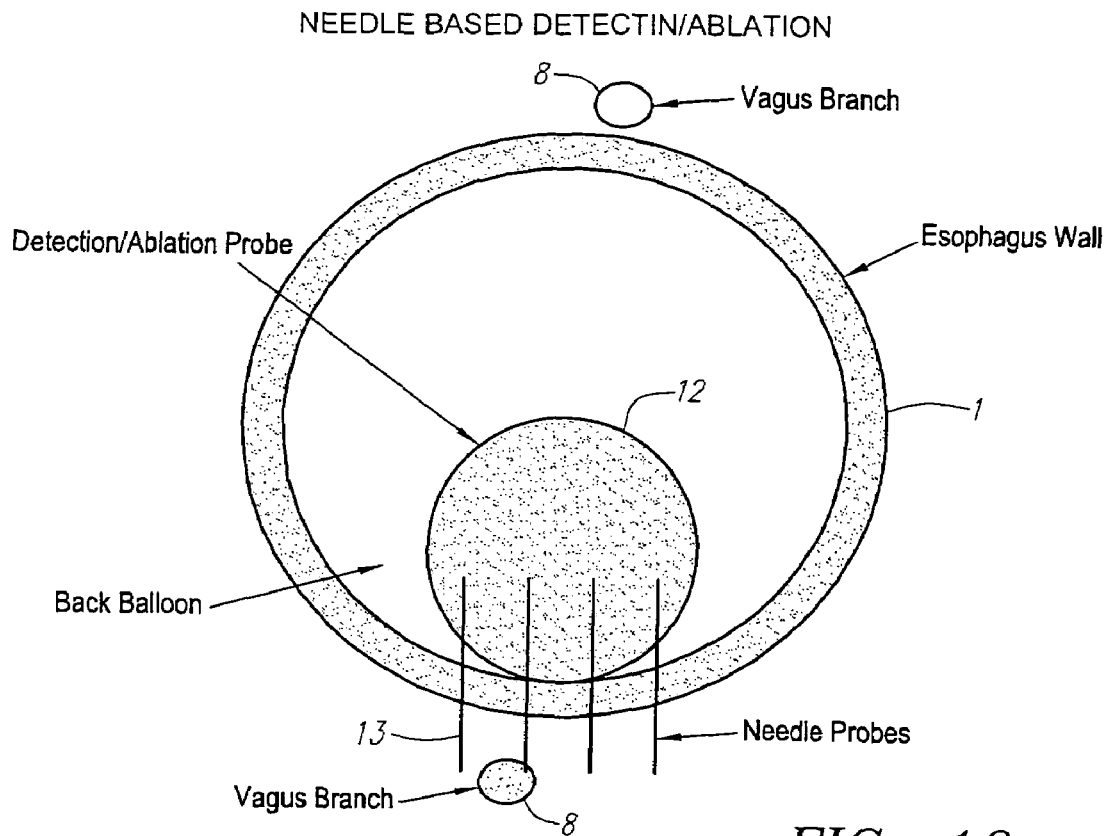
FIG. 10 illustrates the use of still another ablation device to locate and interrupt the vagal nerve.
Figure 11:
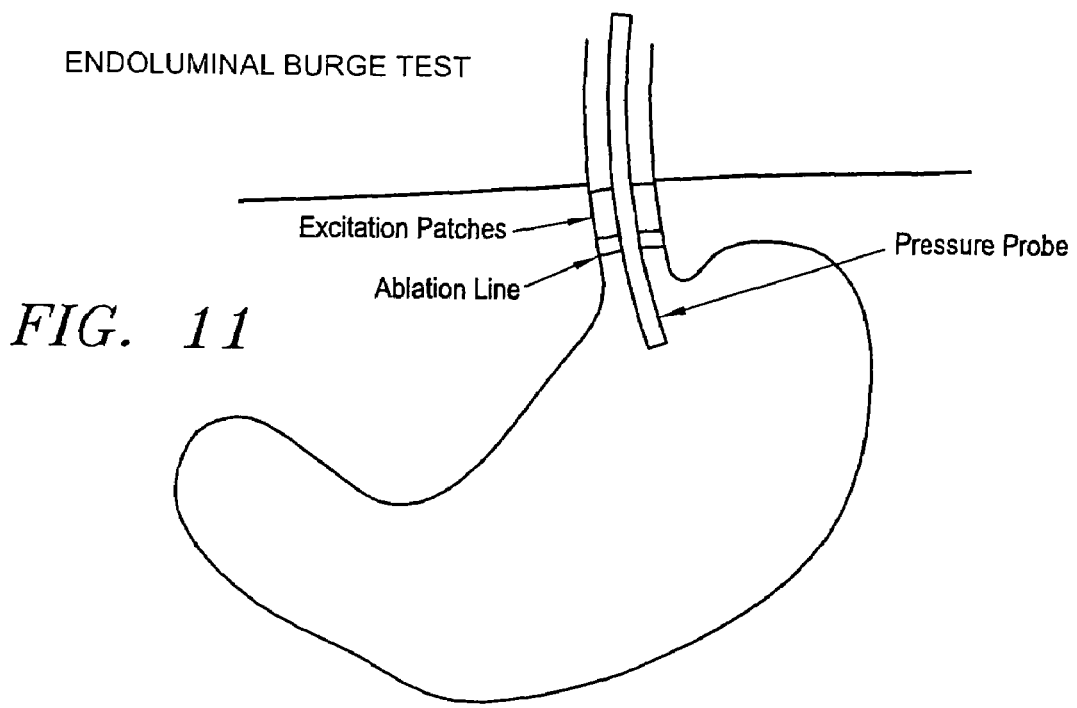
FIG. 11 illustrates an endoluminal burge test which can be used to determine the extent of ablation accomplished.

FIG. 10 illustrates an alternative sector-specific ablation device in which needle probes 13 are activated by device 12 to locate and ablate the vagal nerve in the manner described above. If a patient can obtain the desired benefit of obesity reduction by ablating the two main vagus branches 8, the procedure is simplified and the amount of ablation necessary is reduced. On the other hand, as shown in FIG. 8, if multiple ablation levels 14 are found to be necessary to provide the desired benefit to the patients, more than one ablation can be performed.

If the patient's anatomy makes it desirable, an ablation device 5 can be provided with an energy delivery component 15 which is adjustable such that energy can be delivered perpendicularly to the probe or at an angle to the probe.

When a needle probe is used to deliver energy according to the present invention, the device can be provided with temperature sensors such as thermocouples which are disposed in the distal region of the needle probes. The needle probes can be formed of a variety of materials including nickel-titanium alloy. The needle probes can assume a linear or curved shape when deployed. The device may also be provided with means for cooling the treatment site with a suitable fluid such as water, air, or other liquid or gas, to control the temperature at the treatment site. Thus, the temperature sensor can either cause a cooling medium to be provided or shut off the delivery of energy through one or more needle probes.

In a preferred embodiment of the present invention, high intensity focused ultrasound (HIFU) is used to ablate the vagal nerve branches. The HIFU energy can be transmitted transesophageally to ablate the vagal nerves on the outer wall of the esophagus.

Figure 12:
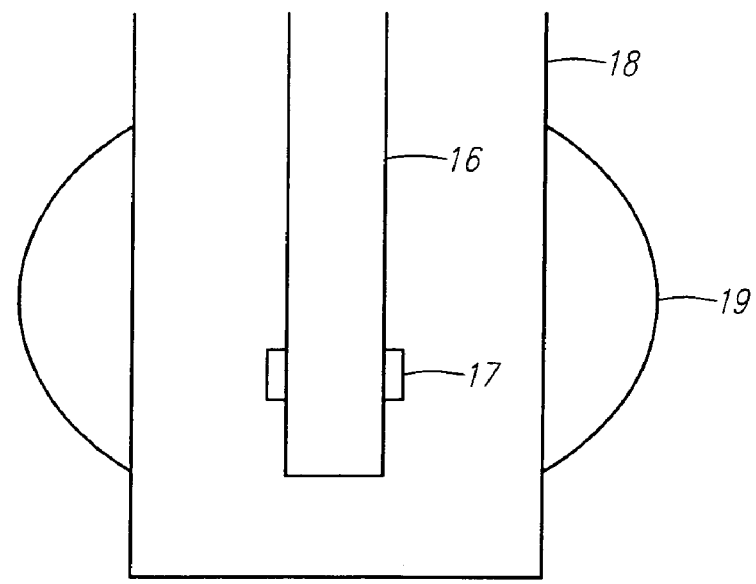
FIG. 12 shows an ultrasound ablating device which may be used according to the present invention.

FIG. 12 illustrates in a diagrammatic form an ultrasound device which can be used according to the present invention. As shown, the device comprises an elongated member 16 which has an ultrasound transducer 17 mounted on its distal region. The elongated member is positioned in a housing 18 which is provided with an inflatable balloon 19. This device may be installed by passing it through the throat and down the esophagus until it reaches its desired location with the balloon 19 deflated. Xray, magnetic resonance imaging, or other known imaging techniques may be used to ascertain the positioning of the treatment device 50, or any other device described herein, in the gastroesophageal region, including axially down the esophagus and rotationally toward the anterior vagus nerve trunk. After rotating the treatment device 50, for example by 180 degrees to target the posterior vagus nerve trunk, the new position of the device 50 may be confirmed by xray, magnetic resonance imaging, or other known imaging techniques. The balloon 19 can then be inflated to position the device and the ultrasound transducer can be activated to transmit energy radially outwardly. Alternatively, a vacuum device can be used to position the housing.

Figure 17A:
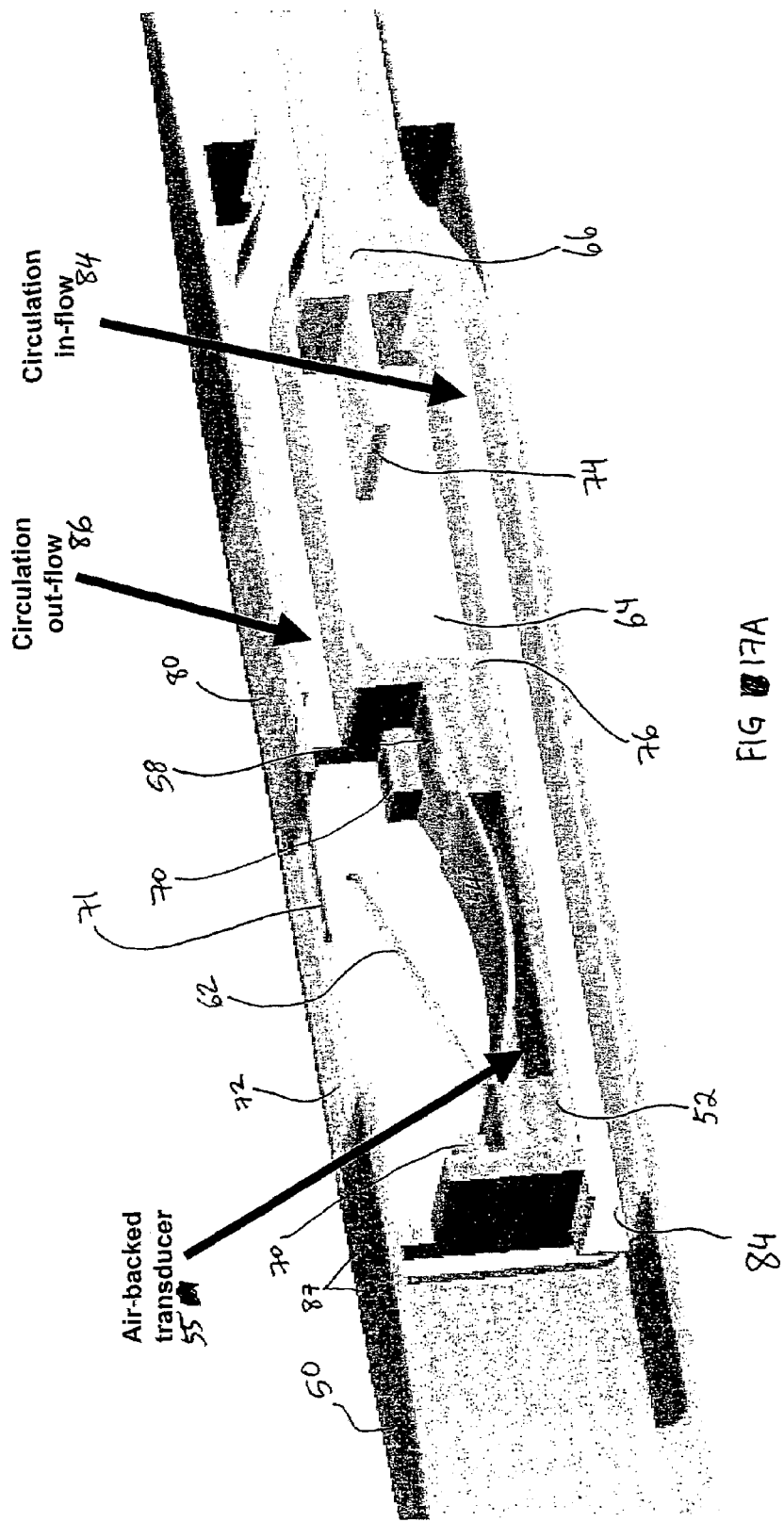
FIG. 17A illustrates a perspective view of a preferred embodiment of the present invention when the ultrasound transducer platform is in a fully lowered position.
Figure 17B:
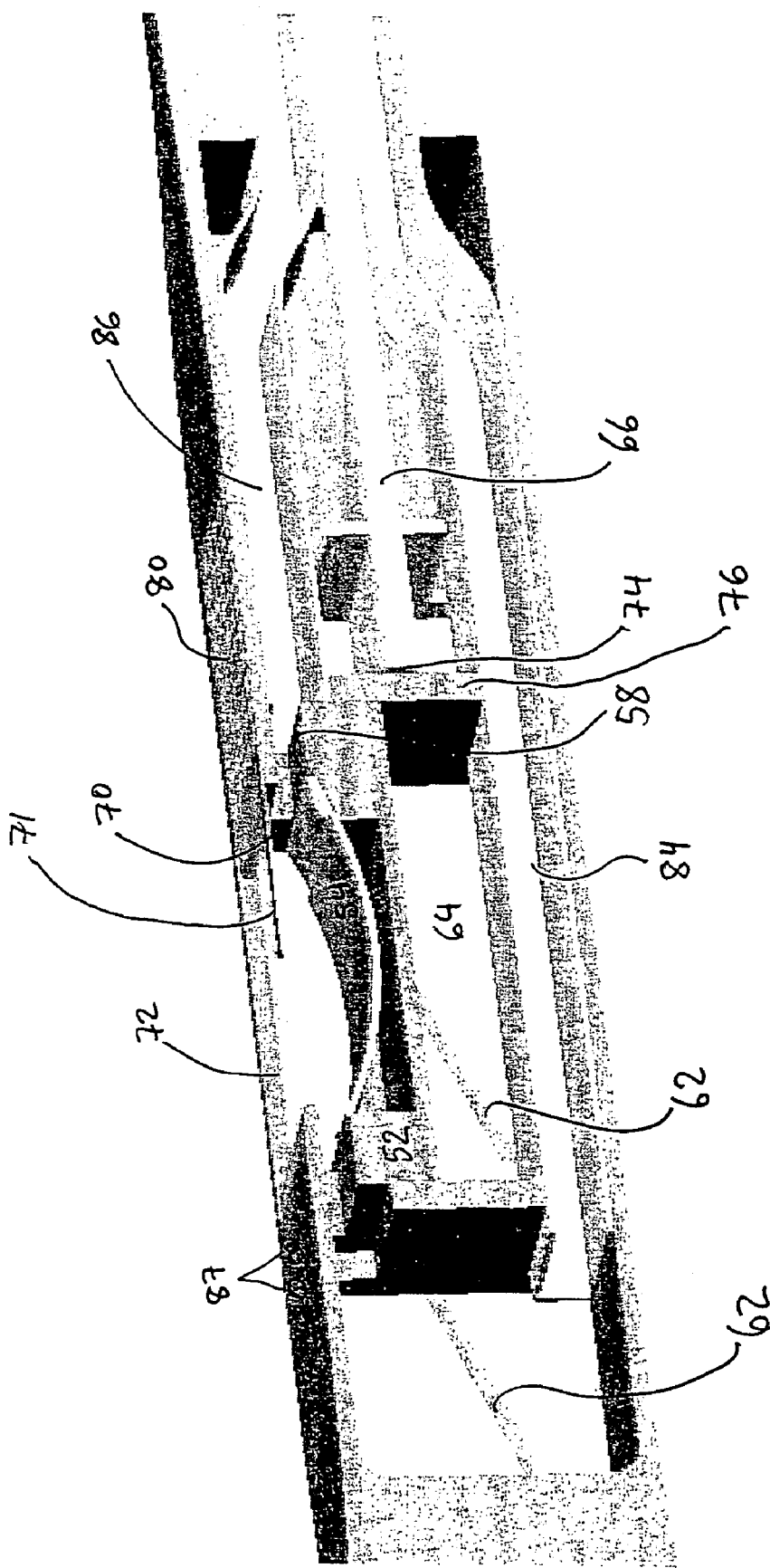
FIG. 17B illustrates a perspective view of a preferred embodiment of the present invention when the ultrasound transducer platform is in a fully raised position.
Figure 20:
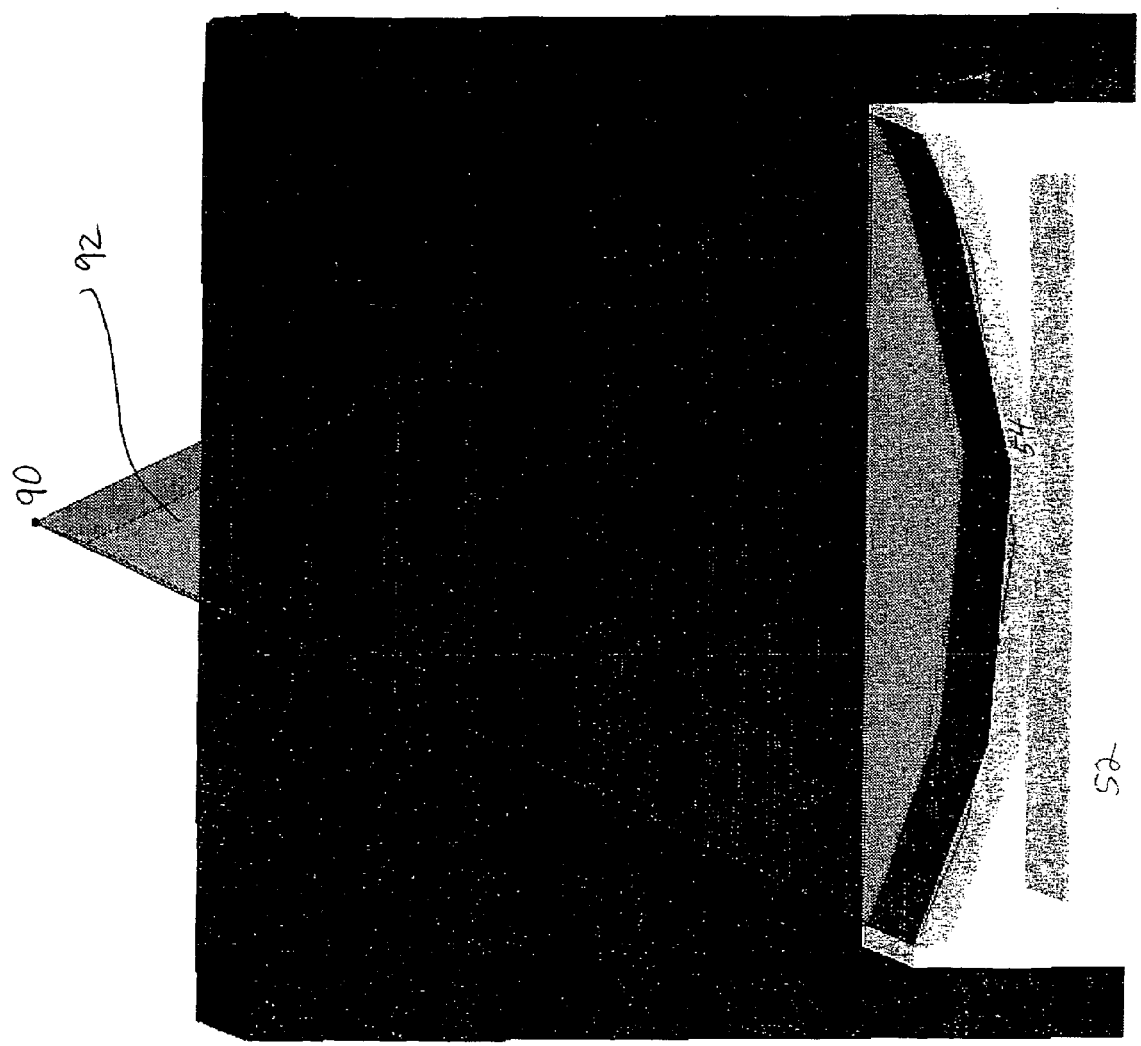
FIG. 20 illustrates an example of the focal point and distribution of energy emitted from the ultrasound transducer.

As shown in FIGS. 17A and 17B, a treatment device 50 is movable along two or three axes. In particular, the treatment device 50 may be moved longitudinally along the axis of the esophagus to a further or closer distal position, transversely along the radius of the esophagus, and rotationally about the axis of the esophagus. These three degrees of freedom are relative to the esophagus. The treatment device 50 has an ultrasound device 54 and preferably treats obesity by disrupting the vagal nerve adjacent the esophagus. In this example embodiment, a movable platform 52 carries a high focus ultrasound (HIFU) transducer device 54. The transducer 54 may be have an air-backing 55, or other types of known transducer backing materials. FIG. 17A illustrates a perspective view of the preferred embodiment when the platform 52 is in a fully lowered position, while FIG. 17B illustrates a perspective view when the platform 52 is in a fully raised position. Of course, the ultrasound transducer 54 may move anywhere between the fully raised position and the fully lowered position. Thus, the platform 52 may move the ultrasound transducer 54 closer to or farther from a treatment window 72 so as to control the focal point of the energy output from the ultrasound transducer 54. As the ultrasound transducer 54 moves farther from the treatment window 72, the focal point of the energy from the ultrasound transducer 54 moves closer to the wall of the esophagus. FIG. 20 illustrates an example of the focal point 90 and distribution 92 of energy emitted from the ultrasound transducer. Thus, the focal point 90 is adjustable. Preferably, the focal point 90 is directed at the site of a vagal nerve and away from the esophagus wall.

FIG. 18 illustrates a perspective view of an example embodiment of the transducer platform 52. The platform 52 preferably carries a high intensity focused ultrasound transducer 54 and an ultrasound imaging transducer 56. The ultrasound imaging transducer 56 performs diagnostic imaging for monitoring the formation of lesions in the esophagus and for defining the outside of the esophagus for the purpose of locating the vagal nerve. The ultrasound imaging transducer 56 can be any known type of imaging transducer such as those that are mechanically based (e.g., rotating and pivoting transducers) or piezo electrically based phased arrays, which have, for example, 128 imaging transducers.

The platform 52 also may include circulation channels 58 for allowing fluid, such as saline, to flow into the device and around the ultrasound transducer 54 so as to improve the acoustic characteristics of the ultrasound transducer 54 or to cool the transducer 54. Even though the transducer 54 is illustrated as having a curved surface, the ultrasound transducer 54 may have any geometry, size, shape and curvature as appropriate.

The platform 52 has one or more guide rails or guide bosses 60, which couple to guide slots 62 of the position actuator 64 shown in FIG. 19, which illustrates a perspective view of an example embodiment of the position actuator 64. Because the guide bosses 60 ride in upward slanted guide slots 62, movement of the distal end 88 of the position actuator 64 toward the platform 52 causes the platform 52 to rise toward the treatment window 72. The upper limit stops 70 on the platform 52 create an upper limit of motion for the platform 52. Of course, variations are also contemplated. For example, the guide slots 62 can be in a falling configuration so that movement of the distal end 88 of the position actuator 64 toward the platform 52 causes the platform 52 to retreat from the treatment window 72. As another example, guide bosses 60 and guide slots 62 may be replaced by any other known mechanism, such as gears, levers or a set of guide rails, to translate the platform 52 toward and away from the treatment window. The guide bosses 60 may be on two or more sides of the platform 52, which would require guide slots 62 on two or more corresponding sides of the position actuator 64. The upper limit stops 70 could hang from the inner surface of the wall having the treatment window 72 instead of being on the platform 52.

As shown in FIG. 19, the position actuator 64 has an elongate member 66 so the physician can push the actuator 64 distally or pull the actuator 64 proximally. A forward stop 74 defines the furthest distal position that the position actuator 64 may be moved.

Turning to FIG. 17A, the platform 52 is shown in its fully lowered position. As such, the forward stop 74 of the position actuator 64 is not engaged with corresponding stop 76 in treatment device 50. FIG. 17A also illustrates a nerve mapping device 80, which is preferably a 10×10 constant current impedance grid for nerve mapping. A thermocouple 71 to monitor the mucosal layer may also be provided on the outer surface of the treatment device 50.

An inflow channel 84 and outflow channel 86 may be provided so that fluids, such as saline, may flow through the treatment device 50. Additionally, optional micro holes 87 may be provided in the wall of the treatment device 50 to facilitate the flow of fluids into and out of the device 50.

Comparing FIG. 17A to FIG. 17B, one will see that the position actuator 64 in FIG. 17B is fully inserted so that the forward stop 74 has engaged corresponding stop 76, and the platform 52 is fully raised. Therefore, in this example preferred embodiment, moving the position actuator 64 distally relative to the treatment device 50 causes the platform 52 to move toward the treatment window 72. Conversely, in this example preferred embodiment, moving the position actuator 64 proximally relative to the treatment device 50 causes the platform 52 to move away from the treatment window 72. Thus, the treatment device 50 permits the position of the ultrasound transducer 54 relative to the treatment window 72, and thus, the esophageal wall, to be adjusted. The adjustable positioning of the ultrasound transducer 54 along this radial axis permits control over the focusing of the energy emitted from the ultrasound transducer 54 onto the vagal nerve in the region of the esophagus while avoiding injury to the esophageal wall.

Besides moving transversely along the radial axis of the esophagus, the platform 52 and ultrasound transducer 54 may be moved along the longitudinal axis of the esophagus to a further or closer distal position. Because the ultrasound transducer 54 can be moved longitudinally, e.g., closer or further from the stomach, the treatment device 50 can be more accurately positioned to ablate or otherwise disrupt the vagal nerve. Moreover, the treatment device 50 may be used to deliver ablating energy to one vagal nerve branch in a transesophageal manner, and then moved to another vagal nerve branch for further disruption of the vagal nerve system or for testing the completeness of the prior disruption of the vagal nerve.

A preferred method of disrupting the vagal nerves is as follows: First, a treatment device 50, or any other device described herein, is positioned at the appropriate location in the esophagus, preferably with the assistance of xray, magnetic resonance imaging, or other known imaging techniques. Such imaging techniques may be used to properly position the treatment device axially down the esophagus and rotationally toward the anterior vagus nerve trunk. Then the inner esophagus is cooled and the ablation depth is adjusted with an imaging crystal along a radial line of the esophagus. High level energy is emitted from the treatment device, such as from a HIFU transducer, to ablate and disrupt the anterior vagal nerve branch. Then the treatment device is rotated by 180 degrees to target the posterior vagus nerve trunk, where the new position of the treatment device may be confirmed by xray, magnetic resonance imaging, or other known imaging techniques. Once the new position of the treatment device is confirmed as being appropriate, the ablation depth is adjusted with an imaging crystal along a radial line of the esophagus and high level energy is emitted from the treatment device to ablate and disrupt the posterior vagal nerve branch.

Figure 13A:
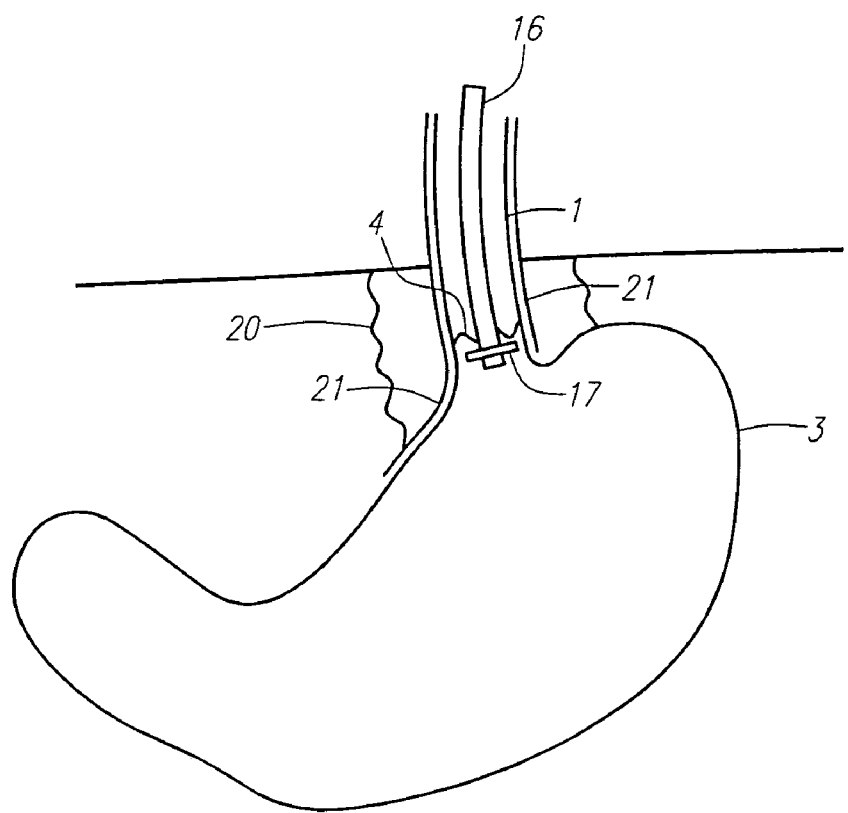
FIG. 13A illustrates an ultrasound device installed in the esophagus.

FIG. 13A is a diagrammatic illustration of an ultrasound transducer installed in the esophagus. As shown in this figure, the transducer device 16 is installed in the esophagus 1 in the region of the Z-line 4. The subhiatal fat ring 20 is also shown. When the transducer 17 is activated, ablating energy will be radiated through the wall of the esophagus to ablate the vagal nerve branches 21 which are also shown diagrammatically.

Figure 13B:
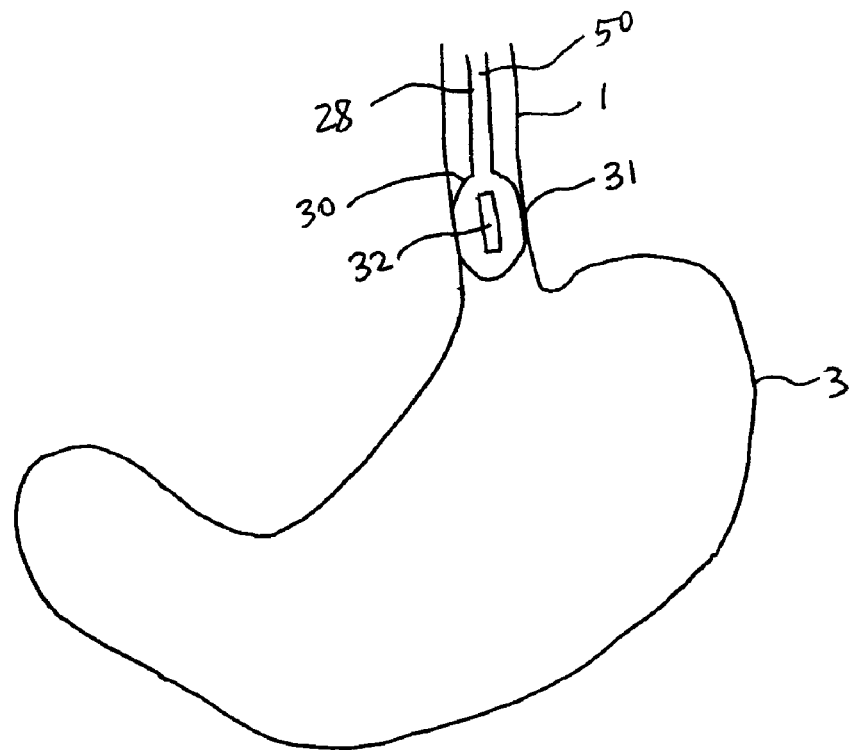
FIG. 13B illustrates the stomach and esophagus with an elongate device with a D-shaped distal tip.
Figure 13C:
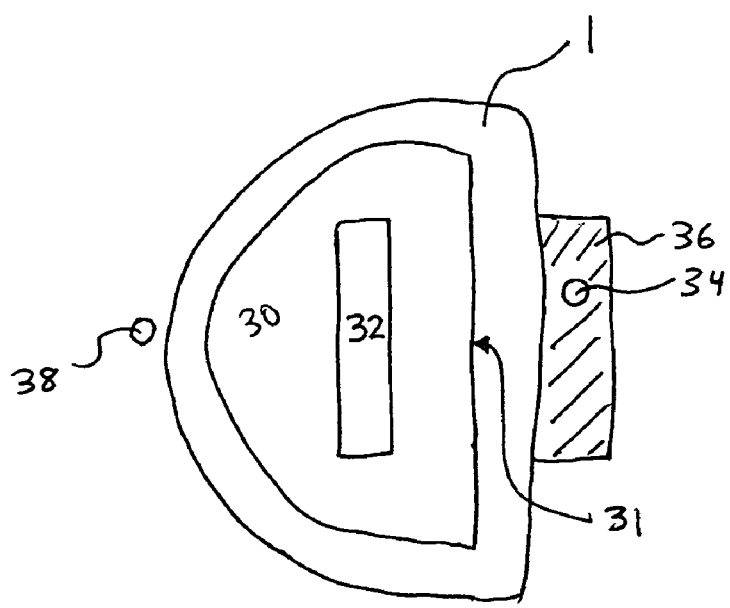
FIG. 13C illustrates a cross section of the esophagus of FIG. 13B to show the D shaped distal tip inside the esophagus.

Although the esophagus is generally illustrated anatomically as a generally cylindrical tube, in its relaxed condition it assumes a more elliptical configuration which can be characterized as floppy. In other words, somewhat like a sock before it is put upon a foot, it does not assume a generally circular configuration unless it contains food or other object, but otherwise has a configuration in which the opposing walls of the esophagus are closer together than they would be when in a circular configuration. For example, FIG. 13B illustrates the stomach 3 and esophagus 1 when an elongate device 28 having a D-shaped distal tip 30 is in place in the esophagus 1. The elongate device 28 is preferably thin, flexible and torqueable. The "D" shape of the distal tip 30 causes the esophageal wall to take on a D shape, with a flat portion 31, as further illustrated in the cross section illustration of FIG. 13C. FIG. 13C illustrates a cross section of the esophagus 1 when the D-shaped distal tip 30 is in place. A HIFU transducer 32 is preferably inside the D-shaped distal tip. By positioning the HIFU transducer 32, which is preferably directed to focus its energy at the flat portion 31 of the D, there is an ablation zone 36 that encompasses the anterior vagal nerve 34. By rotating the D-shaped distal tip 30, the ablation zone can include the posterior vagal nerve 38 or a vagal nerve branch. Thus, when the treatment device 50 is inserted into the esophagus, a cross section of the esophagus would preferably be D-shaped, where the focal point of the energy would be directed in the direction of the flat portion of the "D."

Figure 14:
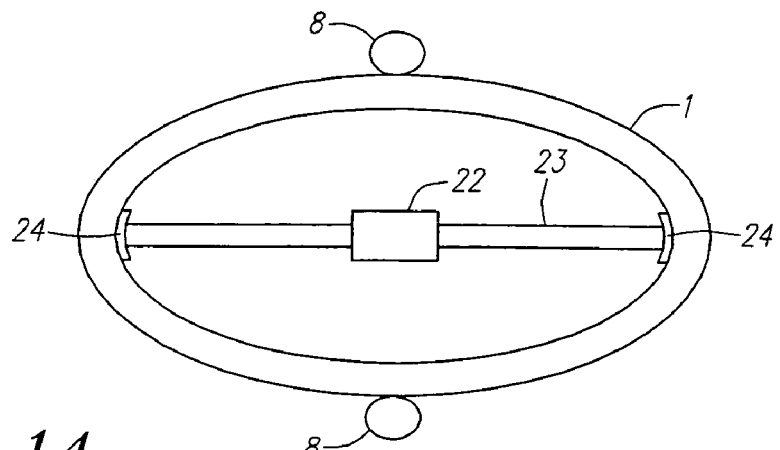
FIG. 14 illustrates an ablation device installed in the esophagus in a manner which shows the esophagus held in its naturally relaxed configuration by a transducer device.
Figure 15:
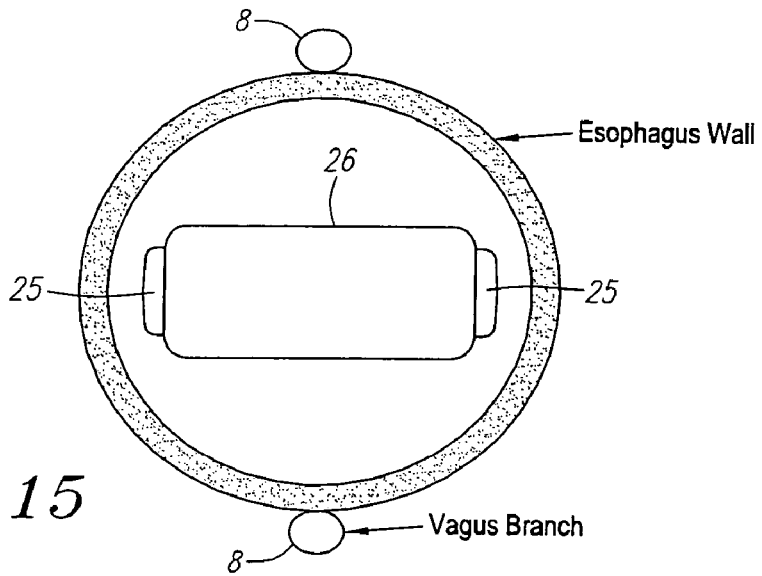
FIGS. 15 and 16 illustrate an alternative to the device shown in FIG. 14.
Figure 16:
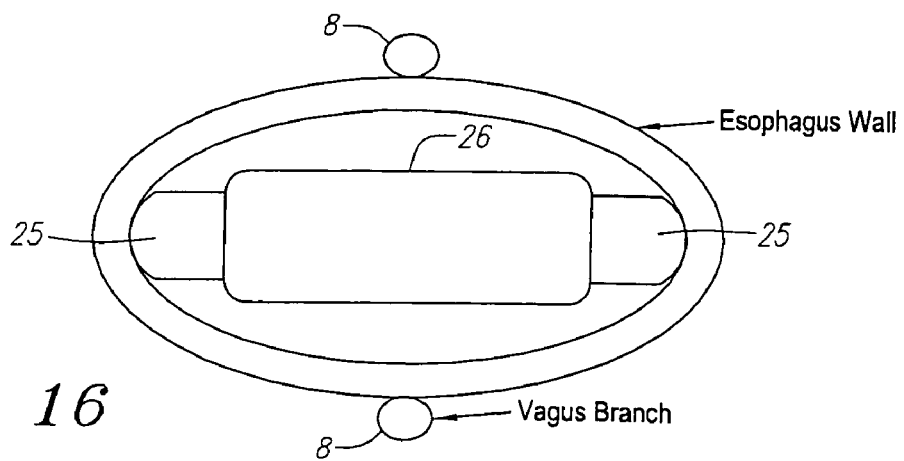

In FIG. 14, esophagus 1 with vagal nerve branches 8 on its outer wall is provided with a transducer 22 which has radially extending struts 23. Each of these struts 23 has a rounded portion 24 at its distal end. The struts 23 and 24 serve to hold the esophagus in its relaxed generally elliptical shape and to hold the transducer 22 in the desired location as well. In an alternative embodiment illustrated in FIGS. 15 and 16, balloons 25 mounted on the side of the transducer-containing device 26 are implemented to hold the esophagus in a more ellipitical shape. When these types of devices are used, the transducer device 22 or 26 could be constructed to direct ultrasound energy towards the vagal nerve branches 8 in one direction or in two directions. FIG. 15 shows the balloons 25 in the deflated state and FIG. 16 shows the balloons in the inflated state.

Ultrasound heating technology, including high-intensity ultrasound and HIFU are well understood. For example, Chapter 12, entitled "Ultrasound heating technology," of "Thermo-radiotherapy and Thermo-chemotherapy," vol. 1, edited by Seegenschmiedt, Fessenden and Vernon, contains a thorough explanation of the use of ultrasound in thermal therapy. This chapter is incorporated by reference herein.

Having explained various methods and apparatuses for treating obesity by disrupting the vagal nerve transesophageally, the present invention is, in general, directed to testing whether the vagal nerve, preferably in the region of the esophagus, has been disrupted and testing the amount of disruption to the vagal nerve.

One example embodiment of the present invention is to use the treatment device 50 described above, where the treatment device 50 is adapted to deliver energy at two or more levels: a high energy level sufficient to disrupt a gastric vagal nerve and a low energy level sufficient to stimulate a gastric vagal nerve without disrupting the nerve. The ultrasound energy levels may be described by its spatial-peak-temporal-average intensity (Ispta), which is measured in $mW/cm^2$ or $W/cm^2$. For example, a low energy level exposure includes the range of about 50 $mW/cm^2$ to 50 $W/cm^2$, and preferably is between about 500 $mW/cm^2$ to 5 $W/cm^2$. A high energy level exposure includes the range of about 50 to 5000 $W/cm^2$, and preferably is between about 300 to 3000 $W/cm^2$. The ultrasound exposure time may range from a few seconds (for example, one to 30 seconds) to minutes (for example, up to 60 minutes and preferably not to exceed five minutes). The shorter the exposure time, the higher the Ispta intensity needs to be for the desired treatment effect. To stimulate the vagal nerve, one may alternatively try a high energy level exposure, but for a shorter exposure time. The ultrasound frequency range preferably is about two to ten MHz, and more preferably is about three to eight MHz.

A preferred example method of the present invention is, generally, to disrupt the gastric vagal nerve transesophageally and to test whether the vagal nerve has been disrupted. Optionally, the method would determine the amount of disruption. One example method involves the steps of introducing the treatment device 50 into the esophagus, positioning its source of energy, e.g., an ultrasound transducer 54, at a location below the diaphragm, delivering energy from the ultrasound transducer 54 at a high energy level, which means an energy level sufficient to disrupt a vagal nerve located outside the esophagus wall, and then testing the disruption of the vagal nerve. There are numerous ways to test the disruption of the vagal nerve, all of which are contemplated for use with the present invention.

For example, the physician may retract the treatment device 50 away from the location at which the high level energy was directed and preferably about one centimeter to an inch further away from the stomach. Then the treatment device 50 is used to deliver a lower level energy from the ultrasound transducer 54 to another portion of the vagal nerve. By using a lower level energy, meaning an energy level sufficient to stimulate the vagal nerve without disrupting the nerve, one can stimulate the vagal nerve at a location not disrupted by the high level energy so that one can test whether the vagal nerve was disrupted and how much it has been disrupted.

To test whether the vagal nerve was disrupted and potentially how much it has been disrupted, several different methods may be used. For instance, one may use a pressure transducer in the stomach to measure the pressure in the stomach before and after delivering the lower level energy to the vagal nerve, and then compare the pressures to see if the pressure changed substantially in response to stimulation of the vagal nerve. If the pressure does not change substantially, it is presumed that the vagal nerve has been disrupted completely or substantially completely. Greater pressure changes in the stomach indicate that the degree of disruption of the vagal nerve may be lesser.

As another example, one may apply a dye agent, such as Congo Red, into the stomach after delivery of the lower level energy to stimulate the vagal nerve and measure the amount of time required for the dye to change from a red color to a black color. If the vagotomy was complete, Congo Red would require approximately 10-20 minutes to change to a black color. If the vagotomy was significantly incomplete, Congo Red would change much more rapidly to a black color.

As yet another example, one may use a pressure transducer in the stomach to measure the pressure in the stomach before and after stimulating the vagal nerve. The pressure transducer allows one to determine the amount of change in pressure, if any, as a result of the stimulation of the vagal nerve. One may conclude that the vagal nerve was completely disrupted if the pressure in the stomach does not change in response to stimulus of the vagal nerves or the vagal centers of the brain. On the other hand, greater pressure changes may indicate less disruption of the vagal nerve. Instead of analyzing the change in pressure, one may be able to determine that the vagal nerve has not been disrupted if the pressure in the stomach after vagal nerve stimulation falls within the normal range of pressures for intact vagal nerves. Analyzing the change in pressure is preferred over merely measuring the pressure.

Still another example of a method for determining whether the vagal nerve was disrupted and the amount of disruption includes measuring a gastric mucosal pH of the stomach after stimulating the vagal nerve or the vagal centers in the brain. Any known device and method for measuring the gastric mucosal pH of the stomach may be used, such as an intraluminal combination electrode. If the gastric mucosal pH is less acidic than normal, e.g., pH of 6, one may conclude that the vagal nerve has been disrupted. Greater disruption to the vagal nerve may result in a smaller acidic response in the stomach mucosal.

As still another example, one may measure the pancreatic polypeptide response to sham feeding and/or phamacological stimulation. See Nagammapudur, S. et al., A Safe and Non-invasive Test for Vagal Integrity Revisited, Arch. Surg., Vol. 137, August 2002, pp. 954-957, the entirety of which is incorporated herein by reference. A rise of greater than fifty percent in the pancreatic polypeptide level within thirty minutes of sham feeding is a strong indicator of vagal integrity. Pancreatic polypeptide response is known to be biphasic, as an early response occurs ten to thirty minutes after vagal stimulation and a prolonged secondary response occurs after thirty minutes to six hours.

As another example, the Burge test may be used. The Burge test uses an esophagus-encircling vagal stimulating electrode placed through an open procedure and depends on a motility response. See Burge, H. et al., "Method Of Testing For Complete Nerve Section During Vagotomy," British Medical Journal, Mar. 15, 1958, pp. 615-618; Burge, H. et al., "The Technique Of Bilateral Selective Vagotomy With The Electrical Stimulation Test," Brit. J. Surg., Vol. 56, No. 6, June 1969, pp. 452-460, both articles of which are incorporated herein in their entirety. The Burge test preferably empties the stomach, applies 10-50 volts to the vagal nerves, and then measures the change in gastric pressure.

A Burge test modified to use a balloon or inflatable cuff, as proposed by T. P. J. Hennessy, may also be used. See Hennessy, T. P. J. et al., "An improved preoperative test of vagal section, Annals of the Royal College of Surgeons of England," Vol. 61, 1979, pp. 474-476, which article is incorporated herein by reference in its entirety. The modified Burge test, also referred to as the strain gauge test, uses cheaper equipment than the Burge test. An example of the Burge test follows. The patient is given oral diazepam and then anaesthesized. A large bore gastric tube is inserted into the stomach with an inflatable cuff lying in the lower esophagus. A Whitney mercury-in-rubber strain gauge is sutured to the anterior stomach wall and then connected via a Parks plethysmograph to a pen recorder. One then occludes the distal stomach with a soft clamp, inflates the cuff, and introduces air into the stomach. Semicircular electrodes are placed around the esophagus, or if open surgery is not contemplated, an electrical stimulus may be applied to the vagal nerve from within the esophagus. For example, an electrical stimulus of 45 volts at 90 c/s with a pulse width of 10 ms is applied for 20 seconds using a square wave stimulator. If the vagal nerves are intact, the simulus causes the stomach to distend, which is shown as a deflection on the strain gauge. A strain response of less than that produced by the introduction of 40 ml of air may not be significant. In other words, if the response is less than the deflection produced by the addition of 40 ml of air, the vagotomy is likely complete.

The Grassi test may be used and employs the potentiating interactions between vagal tone and histamine. The pH of the gastric mucosa is checked with a pH meter connected with a glass electrode that slides over a large surface of the gastric mucosa and to a reference electrode on the oral mucosa. By comparing the pH of the gastric mucosa before and after a vagotomy, with cleansing of the mucosa before the vagotomy and injection of an augmented dose of histamine (0.024 milligrams per kilogram of histamine bichloridrate) after the vagotomy, one may determine whether the pH after the vagotomy is greater than 5.5. See Grassi, G. et al., "Intraoperative Relation Of Gastic Secretion Acidity And Complete Vagotomy," Surgery, Gynecology & Obstetrics, Vol. 134, January 1972, pp. 35-38, which is incorporated herein in its entirety.

Having discussed various alternative methods for testing the completeness of the vagotomy, there are alternative embodiments for stimulating the vagal nerve. One alternative to using the treatment device 50 to output ultrasound energy at a low level to stimulate the vagal nerve is to use a known device that can apply an electrical stimulus to the vagal nerve. Such devices may include probes or needles carrying an electrical voltage.

Instead of delivering a lower level energy to stimulate the vagal nerve, one may introduce to the patient a substance such as PCP-GABA that stimulates gastric activity by acting on vagal centers in the brain. Then one would measure the gastric mucosal pH of the stomach after delivery of the drug or substance. If the gastric mucosal pH is less acidic than normal, e.g., pH of 6, one may conclude that the vagal nerve has been disrupted. The less acidic the stomach mucosal, the more disruption there is to the vagal nerve. PCP-GABA and its use to stimulate gastric acid secretion by acting on vagal centers in the brain is described in Goto, Y. et al., "A New Intraoperative Test for Completeness of Vagotomy: The PCP-GABA (Beta-Parachiorophenol-Gamma-Aminobutyric Acid) Test," The American J. of Surgery, Vol. 147, January 1984, pp. 159-163, which article is incorporated herein in its entirety. Alternatively, one may use a pressure transducer in the stomach and analyze any pressure change in the stomach, or any of the other methods for analyzing the disruption of the vagal nerve.

As another alternative to delivering a lower level energy to stimulate the vagal nerve, one may apply an electrical stimulus to the vagal nerve to stimulate it. One may monitor the stomach for acid changes in the mucosa, pressure changes in the stomach, or any of the other methods for analyzing the disruption of the vagal nerve.

As yet additional alternatives to delivering a lower level energy to stimulate the vagal nerve, one may introduce to the patient other known stimulants such as insulin, 2-deoxy-glucose, neurotransmitter amino acid, and histamine. 2-deoxyglucose, which displaces glucose intracellularly, was proposed by Cole. See Cole, "An Intra-operative Test for the Completeness of Vagotomy, Am. J. Surg., Vol. 123, 1972, pp. 543-44, which is incorporated herein in its entirety.

The insulin test first described by Hollander is another test that may be used. This test examines the gastric acid secretion normally evoked by insulin induced hypoglycemia when the vagal nerves are intact. A comparison of the acid response to insulin before and after vagotomy reveals the effect of vagotomy on acid secretion. An increase in acid concentration of at least twenty mEq. per liter above basal levels within two hours after giving insulin to the patient indicates an incomplete vagotomy. A rise of 10 mEq. per liter is considered acceptable if the spontaneous gastric secretion is anacid. Patients having intact vagal nerves generally have a positive gastric acid response within forty-five minutes of insulin administration. See Bell, P. R. F., "The Long Term Effect Of Vagotomy On The Maximal Acid Response To Histamine In Man," Univ. Dept. of Surgery, Royal Infirmary, Sheffield, England, Vol. 46, No. 4, pp. 387-391, and Ross, B. et al., The Insulin Test After Vagotomy, The Univ. Dept. of Surgery, the Royal Infirmary, Sheffield, England, Vol. 46, No. 4, pp. 379-386, both articles of which are incorporated herein by reference in their entirety.

The augmented histamine test, as described by Bell and Kay, is another test that may be used. In doing this test, one introduces a Ncoplex gastric tube through the nose into the stomach and applies constant pump suction to empty the stomach. 100 milligrams of mepyramine maleate (Anthisan) is injected intramuscularly, and gastric secretions for the next thirty minutes are collected and discarded. Histamine acid phosphate (0.04 mg. per kilogram of body weight) is injected subcutaneously and three specimens of gastric secretion obtained at fifteen minute intervals. The acid output is measured by titration of a five milliliter portion against 0.1N sodium bydroxide with the use of a Topfer indicator. The last two specimens are added to represent the maximal acid response. Complete vagotomy should cause an immediate reduction of over fifty percent in the maximal acid response to histamine. See Bell, P. R. F., "The Long Term Effect Of Vagotomy On The Maximal Acid Response To Histamine In Man," Univ. Dept. of Surgery, Royal Infirmary, Sheffield, England, Vol. 46, No. 4, pp. 387-391, which is incorporated herein by reference in its entirety. This reduction of more than fifty percent is maintained for at least three years in patients having a complete vagotomy.

In the foregoing specification, the invention has been described with reference to specific embodiments thereof. It will, however, be evident that various modifications and changes may be made thereto without departing from the broader spirit and scope of the invention. For example, each feature of one embodiment or method can be mixed and matched with other features shown in other embodiments and methods. As another example, the order of steps of method embodiments may be changed. Features and processes known to those of ordinary skill may similarly be incorporated as desired. Additionally and obviously, features may be added or subtracted as desired. Accordingly, the invention is not to be restricted, but rather to be given the full scope of the attached claims and their equivalents.

We claim:

1. A method for testing the function of a vagal nerve of a patient, the method comprising:
  positioning an energy delivery device within the esophagus adjacent a vagal nerve, the vagal nerve being located outside the esophagus wall;
  delivering a high level energy from the energy delivery device sufficient to disrupt the function of the vagal nerve;
  delivering a lower level of energy from the energy delivery device to another portion of the vagal nerve;
  determining whether the function of the vagal nerve has been disrupted by measuring the pressure in the stomach after delivering the lower level energy to the vagal nerve.

2. The method of claim 1 further comprising;
  delivering the lower level energy from the energy delivery device to a different portion of the vagal nerve than that to which the high level energy was delivered.

3. The method of claim 2 further comprising determining whether the function of the vagal nerve is completely disrupted.

4. The method of claim 1 further comprising
  measuring the pressure in the stomach before delivering the lower level energy to the vagal nerve; and
  comparing the pressure in the stomach before delivery of the lower level energy to the pressure in the stomach after delivery of the lower level energy.

5. The method of claim 4 wherein the determining step includes comparing the pressure in the stomach before delivery of the lower level energy to the pressure in the stomach after delivery of the lower level energy.

6. A method for testing the function of a vagal nerve comprising:
applying an electrical stimulus to the vagal nerve after delivery of the energy sufficient to disrupt the function of the vagal nerve; and
measuring the pressure in the stomach after applying the electrical stimulus to the nerve.

7. The method of claim 6 further comprising:
measuring the pressure in the stomach before applying the electrical stimulus to the vagal nerve; and
comparing the pressure in the stomach before applying the electrical stimulus to the vagal nerve to the pressure in the stomach after applying the electrical stimulus to the vagal nerve.

8. The method of claim 4 further comprising determining that the function of the vagal nerve is completely disrupted if the pressure in the stomach does not change.

9. The method of claim 6 further comprising determining that the function of the vagal nerve is completely disrupted if the pressure in the stomach before applying the electrical stimulus to the vagal nerve is substantially the same as the pressure in the stomach after applying the electrical stimulus to the vagal nerve.

10. The method of claim 1 wherein the step of determining whether the function of the vagal nerve is disrupted includes measuring a gastric mucosal pH of the stomach.

11. The method of claim 10 wherein the step of determining whether the function of the vagal nerve is disrupted includes introducing PCP-GABA before measuring the gastric mucosal pH of the stomach.

12. The method of claim 2 wherein said different location is obtained by retracting the energy delivery device further away from the stomach.

13. The method of claim 1 wherein the energy is ultrasound.

14. The method of claim 1 wherein the energy sufficient to disrupt the function of the vagal nerve is high intensity ultrasound.

15. The method of claim 1 wherein the energy sufficient to disrupt the function of the vagal nerve is high intensity focused ultrasound.

16. The method of claim 1 wherein the energy is radio frequency energy.

17. The method of claim 1 wherein the lower energy level is delivered by electrodes which are passed through the wall of the esophagus.

18. The method of claim 1 further comprising using electrodes to locate a vagal nerve branch.

19. The method of claim 1 wherein the energy delivery device is introduced into the esophagus through the mouth.

20. The method of claim 1 wherein the energy delivery device is delivered to the esophagus through the nose.

21. The method of claim 1 wherein the lower energy level falls within the range of 500 mW/cm2 and 5 W/cm2.

22. The method of claim 1 wherein the high energy level falls within the range of 300 and 3000 W/cm2.

23. The method of claim 21 wherein the high energy level falls within the range of 300 and 3000 W/cm2.

24. The method of claim 1 further comprising measuring the pancreatic polypeptide response to a sham feeding or a pharmacological stimulation.

25. The method of claim 1 further comprising using the Burge test to apply an electrical voltage to the vagal nerve and determining whether gastric pressure in the stomach changes in response to the electrical voltage.

26. The method of claim 1 further comprising using the Burge test with an inflatable balloon and measuring a distension of the stomach.

27. The method of claim 1 further comprising introducing histamine into the patient and checking the pH of the mucosa of the stomach.

28. The method of claim 1 further comprising introducing PCP-GABA into the patient.

29. The method of claim 1 further comprising introducing insulin into the patient.

30. The method of claim 1 further comprising introducing 2-deoxy-glucose into the patient.

31. The method of claim 1 further comprising introducing a neurotransmitter amino acid into the patient.

32. The method of claim 1 further comprising
obtaining the pressure in the stomach before delivering the higher level energy to the vagal nerve;
delivering the high level energy from the energy delivery device sufficient to disrupt the function of the vagal nerve at a time after obtaining the pressure;
measuring the pressure in the stomach before delivering the lower level energy to the vagal nerve; and
comparing the pressure in the stomach before delivery of the lower level energy to the pressure in the stomach after delivery of the lower level energy.

* * * * *